United States Patent
Mogi

(10) Patent No.: US 12,037,571 B2
(45) Date of Patent: Jul. 16, 2024

(54) METHOD OF PRODUCING CELL STRUCTURE, CARRIER, AND METHOD OF PRODUCING CARRIER

(71) Applicant: YOKOGAWA ELECTRIC CORPORATION, Tokyo (JP)

(72) Inventor: Takeyuki Mogi, Musashino (JP)

(73) Assignee: Yokogawa Electric Corporation, Tokyo (JP)

( * ) Notice: Subject to any disclaimer, the term of this patent is extended or adjusted under 35 U.S.C. 154(b) by 766 days.

(21) Appl. No.: 17/252,977

(22) PCT Filed: May 9, 2019

(86) PCT No.: PCT/JP2019/018605
§ 371 (c)(1),
(2) Date: Dec. 16, 2020

(87) PCT Pub. No.: WO2020/008723
PCT Pub. Date: Jan. 9, 2020

(65) Prior Publication Data
US 2021/0115371 A1    Apr. 22, 2021

(30) Foreign Application Priority Data
Jul. 4, 2018 (JP) ................................ 2018-127773

(51) Int. Cl.
*C12M 3/00* (2006.01)
*B01L 3/00* (2006.01)
(Continued)

(52) U.S. Cl.
CPC ............ *C12M 23/50* (2013.01); *C12M 21/08* (2013.01); *C12M 23/06* (2013.01); *C12M 23/44* (2013.01);
(Continued)

(58) Field of Classification Search
CPC .............................. C12M 23/50; C12M 27/16
See application file for complete search history.

(56) References Cited

U.S. PATENT DOCUMENTS 8,198,086 B2    6/2012  Koga et al.
11,332,704 B2 *  5/2022  Tajima .................. C12M 23/04
(Continued)

FOREIGN PATENT DOCUMENTS

EP    2995381 A1 *  3/2016  ............... B01L 9/06
GB    2400378        10/2004
(Continued)

OTHER PUBLICATIONS

Chinese Office Action dated Jan. 31, 2024 and issued for Chinese patent application No. 201980043430.2 and its English machine translation.

*Primary Examiner* — Nathan A Bowers
(74) *Attorney, Agent, or Firm* — RANKIN, HILL & CLARK LLP

(57) ABSTRACT

A method of producing a cell structure includes applying a magnetic field, in a container (40), to a plurality of culture carriers to arrange the culture carriers. The culture carriers include at least one of a carrier (10) and a cell holding carrier (30), the carrier (10) having a magnetic portion (12), formed only in a part of the carrier (10), and a cell holder (11). The method also includes culturing cells (20) held on the cell holder (11) while maintaining the culture carriers in the arranged state.

12 Claims, 7 Drawing Sheets

(51) Int. Cl.
*C12M 1/00* (2006.01)
*C12M 1/12* (2006.01)
*C12M 3/06* (2006.01)
*C12N 5/00* (2006.01)
*C12N 5/09* (2010.01)
*C12N 11/02* (2006.01)

(52) U.S. Cl.
CPC ........... *C12M 27/16* (2013.01); *C12N 5/0062* (2013.01); *C12N 5/0693* (2013.01); *C12N 11/02* (2013.01); *C12N 2513/00* (2013.01); *C12N 2537/00* (2013.01)

(56) References Cited

U.S. PATENT DOCUMENTS

| | | | |
|---|---|---|---|
| 2004/0248291 A1* | 12/2004 | Yamamoto | C12N 5/0075 |
| | | | 435/325 |
| 2008/0038806 A1* | 2/2008 | Fuhr | C12M 25/16 |
| | | | 435/307.1 |
| 2008/0160622 A1* | 7/2008 | Su | G01N 1/4044 |
| | | | 436/86 |
| 2009/0011494 A1* | 1/2009 | Kishida | C12N 15/87 |
| | | | 435/302.1 |
| 2009/0137018 A1 | 5/2009 | Becker et al. | |
| 2012/0171744 A1 | 7/2012 | Souza | |
| 2014/0186946 A1* | 7/2014 | Davis | C12M 23/20 |
| | | | 435/378 |

FOREIGN PATENT DOCUMENTS

| | | |
|---|---|---|
| JP | 2004-313007 A | 11/2004 |
| JP | 2004313008 | 11/2004 |
| JP | 4517125 B2 | 8/2010 |
| JP | 2012-503492 A | 2/2012 |
| JP | 2013-505728 A | 2/2013 |
| JP | 2017-532971 A | 11/2017 |
| WO | 2005003332 | 1/2005 |
| WO | 2005010139 | 2/2005 |
| WO | WO-2005059506 A2 * | 6/2005 |
| WO | 2010/036957 A1 | 4/2010 |
| WO | 2011/038370 A1 | 3/2011 |
| WO | 2016/069930 A1 | 5/2016 |

* cited by examiner

Provide positive charge    Provide negative charge

Plan view of portion of bottom surface

METHOD OF PRODUCING CELL STRUCTURE, CARRIER, AND METHOD OF PRODUCING CARRIER

CROSS-REFERENCE TO RELATED APPLICATION

The present application claims priority to and the benefit of Japanese Patent Application No. 2018-127773 filed Jul. 4, 2018, the entire contents of which are incorporated herein by reference.

TECHNICAL FIELD

The present disclosure relates to a method of producing a cell structure, a carrier, and a method of producing a carrier.

BACKGROUND

In recent years, attempts have been made to construct cell structures in which cells are organized into desired shapes such as sheets, tubes, and spheres for use in fields such as regenerative medicine, disease modeling, drug efficacy tests, and safety tests.

As a method for organizing cells, patent literature (PTL) 1 discloses introducing a solution (cell suspension) in which adhesive cells are suspended into a culture container that has been surface treated to be cell non-adhesive and allowing the cells to aggregate autonomously to form a spheroid. PTL 2 discloses a method of obtaining a three-dimensional cell structure by first piercing cell cluster spheroids with a needle-like body provided on a substrate, so as to arrange the spheroids in a desired shape, and subsequently culturing in a medium for the arranged spheroids to fuse. Furthermore, PTL 3 discloses a method of forming an aggregate body (cell structure) by attaching magnetic nanoparticles to cells and suspending the magnetized cells by application of a magnetic force.

CITATION LIST

Patent Literature

PTL 1: JP 2017-532971 A
PTL 2: WO4517125
PTL 3: JP 2012-503492 A

SUMMARY

Technical Problem

With the method of PTL 1, however, the structure of the produced organization cannot be controlled. With the method of PTL 2, the production throughput is low, and it is difficult to form small structures. Furthermore, the configuration of the cell structure produced with the method of PTL 3 cannot be freely controlled, and this method is highly invasive to cells.

The present disclosure aims to provide a cell structure production method that can freely control the configuration of the cell structure to be produced, that has high throughput, and that is not invasive to cells.

Solution to Problem

A method of producing a cell structure according to various embodiments includes a step (A) of preparing a plurality of culture carriers including at least one of a carrier and a cell holding carrier, the carrier including a magnetic portion formed only in a part of the carrier and a cell holder configured to hold cells, and the cell holding carrier being formed by cells being held on the cell holder of the carrier, a step (B) of applying a magnetic field to arrange the plurality of culture carriers in a container, and a step (C) of culturing the cells held on the cell holder of the culture carriers while maintaining the culture carriers in an arranged state in the container. This configuration can provide a cell structure production method that can freely control the configuration of the cell structure to be produced, that has high throughput, and that is not invasive to cells.

A carrier according to various embodiments includes a magnetic portion and a cell holder configured to hold cells. The magnetic portion only occupies part of the carrier. Such a carrier can be used in the method of producing a cell structure according to various embodiments.

A method of producing a carrier according to various embodiments is a method of producing a carrier including a magnetic portion and a cell holder configured to hold cells, the magnetic portion only occupying part of the carrier. The method includes forming, in a mold a layer including a sol containing magnetic particles and a layer including a sol having a cell holding property, and solidifying each sol in the mold. Such a production method enables simple production of carriers to be used in the method of producing a cell structure according to various embodiments.

Advantageous Effect

The present disclosure can provide a cell structure production method that can freely control the configuration of the cell structure to be produced, that has high throughput, and that is not invasive to cells.

BRIEF DESCRIPTION OF THE DRAWINGS

In the accompanying drawings:
FIG. 2A illustrates a carrier with a magnetic portion formed on the tip,
FIG. 2B illustrates a carrier with a magnetic portion formed towards one end from the center in the height direction,
and FIG. 2C illustrates a carrier in which the transverse direction is the height direction;
FIG. 3A is an example of a combining carriers that have engaging portions,
and FIG. 3B is an example of combining carriers with different characteristics;
FIG. 7A is a flowchart of an example production method of a first embodiment,
and FIG. 7B is a flowchart of an example production method of a second embodiment.

DETAILED DESCRIPTION

Figure 1:
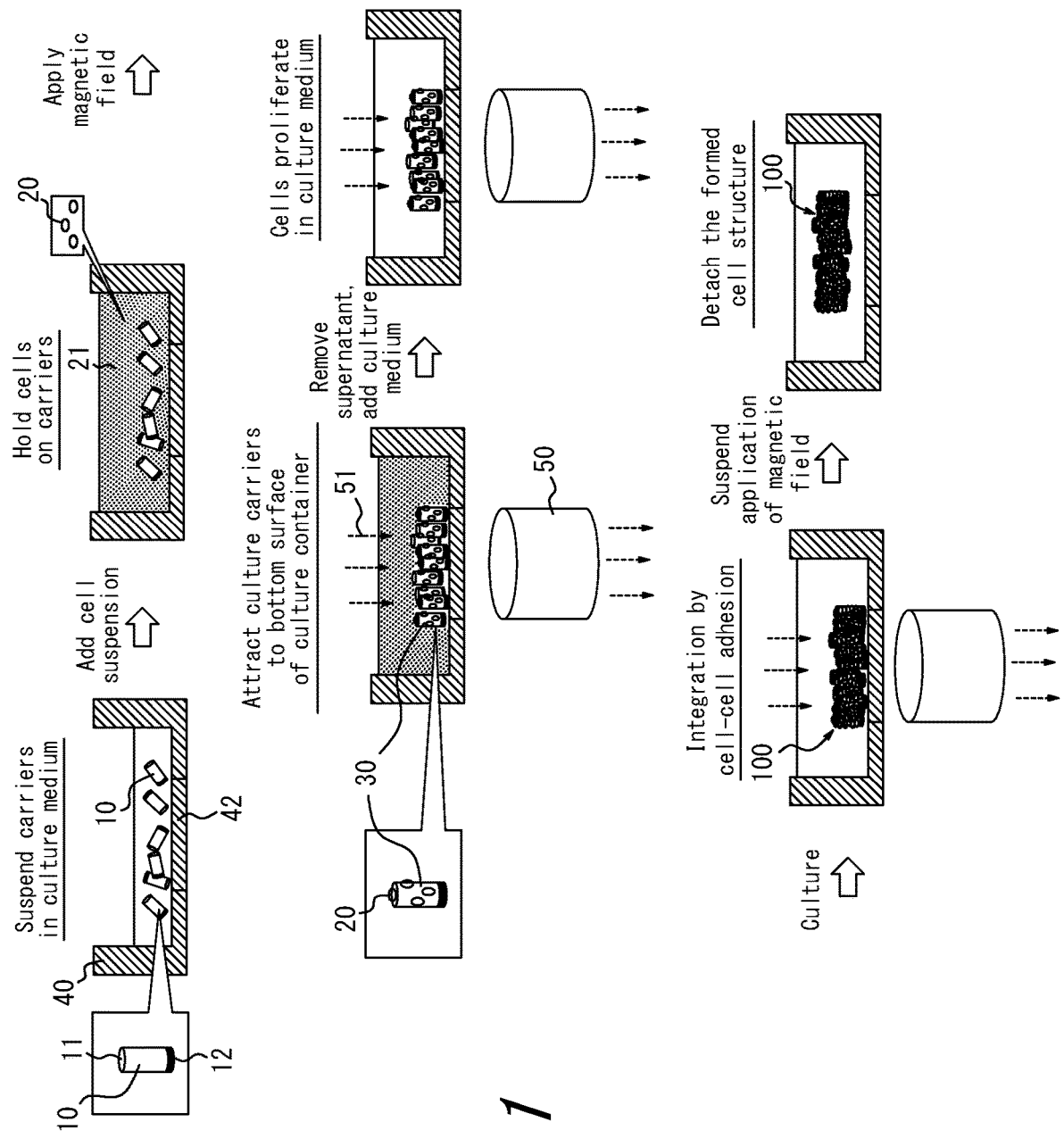
FIG. 1 is a schematic diagram illustrating an example method of producing a cell structure.

In the method of producing a cell structure according to an embodiment, the carrier may be columnar and may include the magnetic portion towards one end from a center in the height direction, and the cell holder may extend in the height direction. A thick cell structure can be produced efficiently when, in this way, the carrier is columnar and includes the magnetic portion towards one end from the center in the height direction, and the cell holder extends in the height direction.

In the method of producing a cell structure according to an embodiment, step (B) may include a step (b1) of applying vibration to the container. The culture carriers can be precisely arranged by application of voltage to the container in this way. Variation in the shape of the cell structure to be produced can therefore be reduced.

In the method of producing a cell structure according to an embodiment, step (B) may include switching the vibration on and off while continuing to apply the magnetic field. When step (B) includes switching the vibration on and off while continuing to apply the magnetic field in this way, the risk of the properly arranged culture carriers becoming misaligned due to the vibration can be reduced.

In the method of producing a cell structure according to an embodiment, step (B) may include setting the magnetic flux density of the magnetic field while the vibration is applied to be lower than the magnetic flux density of the magnetic field before the vibration is applied. When the magnetic flux density of the magnetic field while the vibration is applied is set to be lower than the magnetic flux density of the magnetic field before the vibration is applied in step (B) in this way, the culture carriers that were not arranged as desired can be rearranged efficiently, and variation in the shape of the cell structure to be produced can be further reduced.

In the method of producing a cell structure according to an embodiment, step (B) may include a step (b2) of removing unarranged culture carriers. When unarranged culture carriers are removed in step (B) in this way, the shape of the cell structure can be controlled precisely.

In the method of producing a cell structure according to an embodiment, two or more types of the culture carriers may be used. When two or more types of the culture carriers are used in this way, a cell structure with a complex structure can be produced.

In the method of producing a cell structure according to an embodiment, at least one characteristic may differ between the two or more types of the culture carriers, and the culture carriers may exhibit affinity or repellence towards each other due to the characteristic. When at least one characteristic differs between the two or more types of the culture carriers, and the culture carriers exhibit affinity or repellence towards each other due to the characteristic in this way, a cell structure with a more complex structure can be produced than when the culture carriers are arranged using only a magnetic field, and the culture carriers can be arranged precisely. Furthermore, when the culture carriers exhibit affinity or repellence towards each other, the arranged state of the culture carriers can be maintained more easily.

In the method of producing a cell structure according to an embodiment, the plurality of culture carriers may include engaging portions configured to engage with each other, and step (B) may include engaging the engaging portions with each other to arrange the plurality of culture carriers. When carriers including engaging portions configured to engage with each other are used, and the engaging portions are engaged with each other to arrange the plurality of culture carriers in this way, a cell structure with a more complex structure can be produced than when the culture carriers are arranged using only a magnetic field, and the culture carriers can be arranged precisely. Furthermore, since the engaging portions of the culture carriers engage with each other, the arranged state of the culture carriers can be maintained more easily.

In the method of producing a cell structure according to an embodiment, the container may include a fitting portion, the culture carriers may be configured to fit onto the fitting portion, and step (B) may include fitting the culture carriers onto the fitting portion to align the culture carriers. When the container includes a fitting portion, and the culture carriers are configured to fit onto the fitting portion in this way, a cell structure with a more complex structure can be produced than when the culture carriers are arranged using only a magnetic field, and the culture carriers can be arranged precisely. Furthermore, since the culture carriers are fitted onto the fitting portion, the arranged state of the culture carriers can be maintained more easily.

The method of producing a cell structure according to an embodiment may further include a step (D) of removing the magnetic portion from the cell structure. When the magnetic portion is removed from the cell structure in this way, a cell structure with less material other than cells can be produced.

The method of producing a cell structure according to an embodiment may further include a step (E) of removing the carriers from the cell structure. When the carriers are removed from the cell structure in this way, the portions that was occupied by the carriers become hollow. This enables production of a cell structure with a complex structure, such as a highly oxygen-permeable cell structure with many empty spaces. Furthermore, a cell structure with less material other than cells can be produced.

In the method of producing a cell structure according to an embodiment, step (B) may include applying the magnetic field to a plurality of regions separated from each other in the container and arranging the plurality of culture carriers in the plurality of regions. When the magnetic field is applied to a plurality of regions separated from each other in the container, and the plurality of culture carriers are arranged in the plurality of regions in this way, a plurality of cell structures can be produced simultaneously in one container, enabling cell structures to be produced with high throughput.

A method of producing a cell structure according to an embodiment may include a step (A) of preparing a plurality of culture carriers including cell holding carriers, a step (B) of applying a magnetic field 51 to arrange the plurality of culture carriers in a container, and a step (C) of culturing cells held on the culture carriers while maintaining the culture carriers in an arranged state in the container. This configuration can provide a cell structure production method that can freely control the configuration of the cell structure to be produced, that has high throughput, and that is not invasive to cells. Furthermore, preparation of the plurality of culture carriers including cell holding carriers before step (B) of arranging the culture carriers facilitates the use of two or more types of culture carriers that hold different cell types, or of two or more types of culture carriers that hold cells with different cell ratios.

A method of producing a cell structure according to an embodiment may include a step (A) of preparing a plurality of culture carriers including carriers, a step (B) of applying a magnetic field to arrange the plurality of culture carriers in a container, a step (b3) of holding cells on cell holders of the arranged culture carriers, and a step (C) of culturing the cells held on the culture carriers while maintaining the culture carriers in an arranged state in the container. This configuration can provide a cell structure production method that can freely control the configuration of the cell structure to be produced, that has high throughput, and that is not invasive to cells. Furthermore, arrangement of the culture carriers before the step (b3) of holding the cells makes it unnecessary to manage the operating conditions to avoid adverse effects on cells in step (B) of arranging the culture carriers. This simplifies the operations of step (B).

In the method of producing a cell structure according to an embodiment, at least two types of cells may be included in a cell suspension. When a suspension including at least two types of cells is used in this way, a cell structure including two or more types of cells can be produced.

In the method of producing a cell structure according to an embodiment, step (B) may include arranging the cell holding carriers so that at least a portion of the cells held in adjacent cell holding carriers come into contact with each other. When the cell holding carriers are arranged so that at least a portion of the cells held in adjacent cell holding carriers come into contact with each other in this way, the time required for organization is reduced. Cell structures can therefore be produced with even higher throughput.

In the method of producing a cell structure according to an embodiment, step (b2) may include reusing the removed, unarranged culture carriers in production of cell structures. Reuse of the culture carriers can reduce the cost of producing cell structures.

The mold is an elastic body in the method of producing a carrier according to an embodiment. Since the mold is an elastic body in this production method, the carrier can easily be extracted by deforming the mold after the sols have solidified.

A kit for producing a cell structure according to an embodiment includes culture carriers including at least one of a carrier and a cell holding carrier, the carrier including a magnetic portion formed only in a part of the carrier and a cell holder configured to hold cells, and the cell holding carrier being formed by cells being held on the cell holder of the carrier. Such a kit enables simple implementation of the method of producing a cell structure according to various embodiments.

A kit for producing a cell structure according to an embodiment includes culture carriers and an instruction manual, the culture carrier including at least one of a carrier and a cell holding carrier, the carrier including a magnetic portion formed only in a part of the carrier and a cell holder configured to hold cells, and the cell holding carrier being formed by cells being held on the cell holder of the carrier. Such a kit enables simple implementation of the method of producing a cell structure according to various embodiments.

Embodiments of the present disclosure are described below based on the drawings. Identical reference signs in the drawings indicate identical or similar constituent elements.

[Method of Producing a Cell Structure]

A method of producing a cell structure of the present disclosure includes a step (A) of preparing a plurality of culture carriers each including a magnetic portion formed only in a part of the culture carrier, a step (B) of applying a magnetic field to arrange the plurality of culture carriers in a container, and a step (C) of culturing cells 20 held on the culture carriers while maintaining the culture carriers in an arranged state in the container. When a magnetic field is applied in this way to culture carriers including a magnetic portion only in a part thereof, the culture carriers can be arranged into a desired shape inside a container. When the cells held on the culture carriers are cultured while the culture carriers are in the arranged state, a cell structure organized into a desired shape, such as a sheet, a tube, or a sphere, can be formed. The operation to hold cells on the carriers and the operation to arrange the carriers using a magnetic field are easy and not very invasive to cells. The present method of producing a cell structure therefore enables production of cell structures with high throughput and little invasiveness as compared to when cell clusters are pierced with a needle and arranged, or when the cells themselves are magnetized. Furthermore, in the present embodiment, preparation of the plurality of culture carriers including cell holding carriers before step (B) of arranging the culture carriers facilitates the use of two or more types of culture carriers that hold different cell types, or of two or more types of culture carriers that hold cells with different cell ratios.

The culture carrier used in the method of producing a cell structure of the present disclosure includes at least one of a carrier and a cell holding carrier, the carrier including a magnetic portion formed only in a part of the carrier and a cell holder configured to hold cells (the carrier before cells are held being referred to as a "non-cell holding carrier"), and the cell holding carrier being formed by cells being held on the cell holder of the carrier. The culture carrier may also include carriers other than the non-cell holding carrier and the cell holding carrier.

Cells held on the culture carriers are cultured in step (C) of the method of producing a cell structure of the present disclosure, as described above. Therefore, when the culture carriers arranged in step (B) include the non-cell holding carriers in the method of producing a cell structure of the present disclosure, a step (b3) of holding cells on the cell holders of the arranged non-cell holding carriers can be performed before the cells held on the culture carriers are cultured in step (C).

The method of producing a cell structure of the present disclosure is described in two parts as follows.

(1) A production method including a step (A) of preparing a plurality of culture carriers including cell holding carriers, a step (B) of applying a magnetic field to arrange the plurality of culture carriers in a container, and a step (C) of culturing cells held on the culture carriers while maintaining the culture carriers in an arranged state in the container (First Embodiment).

(2) A production method including a step (A) of preparing a plurality of culture carriers including non-cell holding carriers, a step (B) of applying a magnetic field to arrange the plurality of culture carriers in a container, a step (b3) of holding cells on cell holders of the arranged culture carriers, and a step (C) of culturing the cells held on the culture carriers while maintaining the culture carriers in an arranged state in the container (Second Embodiment).

The method of producing a cell structure of the present disclosure is not limited to the first and second embodiments described below.

First Embodiment

Figure 7A:
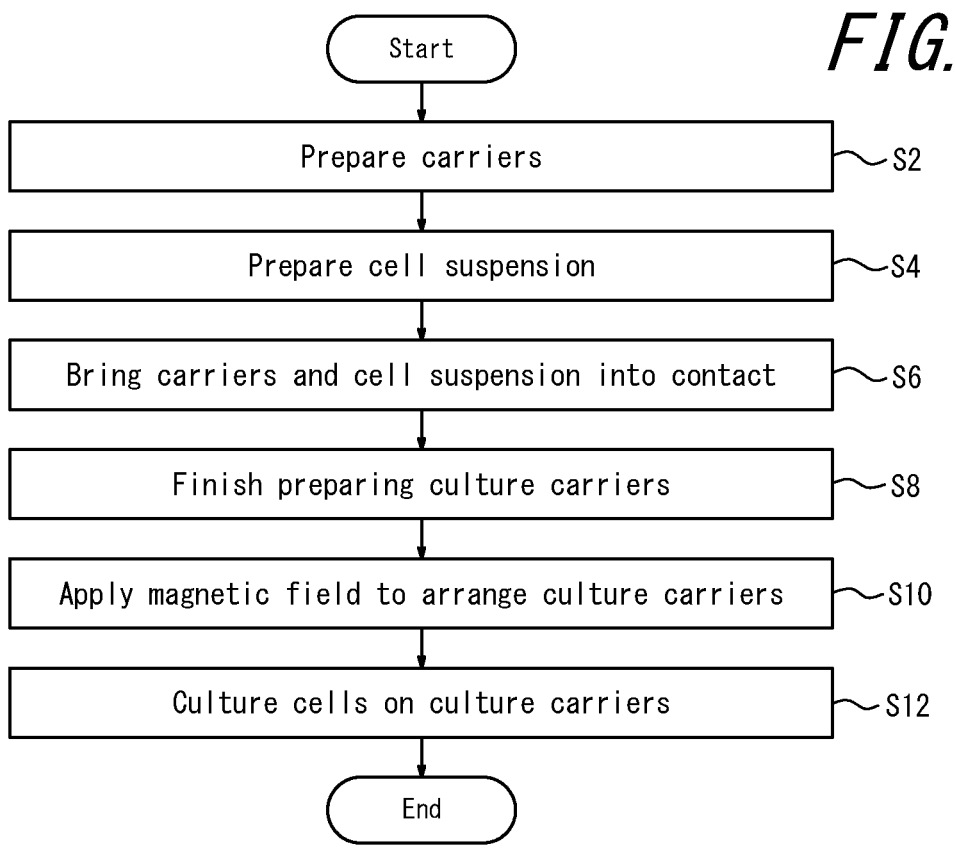
FIGS. 7A and 7B are flowcharts of an example method of producing a cell structure, where

FIG. 1 and FIG. 7A illustrate an example of the flow in a method of producing a cell structure. In the illustrated example, a plurality of culture carriers including cell holding carriers 30 are first prepared in a culture container 40 (container) (step (A)). Next, a magnetic field 51 is applied by bringing a magnet 50 close to the bottom of the culture container 40 from below the outside of the culture container 40 to arrange the plurality of culture carriers that include the plurality of cell holding carriers 30 inside the culture container 40 (step (B)). Subsequently, cells 20 held on cell holders 11 of the cell holding carriers 30 are cultured while maintaining the culture carriers including the cell holding carriers 30 in the arranged state in the culture container 40 (step (C)). Cell-cell adhesion occurs as a result of the culturing, yielding a cell structure 100 in which a plurality of cells 20 are adhered. The magnet 50 is then moved away from the bottom of the culture container 40 to separate the resulting cell structure 100 from the bottom surface 42 of the culture container 40 for collection. Details on each step are provided below.

<Step (A)>

In step (A), a plurality of culture carriers including cell holding carriers 30 are prepared. Specifically, as an example of step (A), a plurality of carriers 10 (non-cell holding carriers) that include the magnetic portion 12 and the cell holder 11 are prepared, as illustrated in FIG. 1. The carriers 10 are then suspended in a cell-compatible liquid, such as a liquid culture medium, in the culture container 40 to create a carrier suspension. Next, a cell suspension 21 in which cells are suspended in a liquid culture medium is added to the suspension of the carriers 10, and cells 20 are held on the cell holders 11, yielding the cell holding carriers 30.

When the cell suspension 21 is used to hold cells 20 on the carriers 10 in this way, culture carriers that hold cells 20 in any state can easily be prepared. Examples of the state of the cells 20 include the activity of the cells 20. The use of culture carriers that hold cells 20 in any state facilitates adjustment of the properties of the cell structure 100 and of the culture time during step (C). When culture carriers including the cell holding carriers 30 are prepared in the same culture container 40 as the culture container 40 used in steps (B) and (C), the apparatus used for producing the cell structure 100 can be simplified. Productivity can also be increased by reducing loss of the culture carriers and reducing the risk of contamination by microorganisms or the like.

The carriers 10 (non-cell holding carriers) can be produced by any method, such as the below-described method of producing carriers. Sufficient non-cell holding carriers 10 for formation of the cell structure 100 in step (C) may be included among the culture carriers prepared in step (A). The method of preparing the culture carriers that include the cell holding carriers 30 in step (A) is not limited to the aforementioned example. Specifically, in step (A), commercially-available cell holding carriers 30 may be purchased to prepare the culture carriers. Alternatively, as described below in the explanation of the method of producing the carriers 10, cells 20 may be mixed with a sol at the time of formation of the cell holders 11. The sol may then be solidified to produce cell holding carriers 30, in which the cells 20 are buried in the cell holders 11, in advance for use as the culture carriers. Cells may also be held by being brought into contact with the cell holders 11 of the carriers 10 using a cell printer, cell spray, optical tweezers, a manipulator, or the like to prepare the culture carriers that include the cell holding carriers 30. Furthermore, the step (S4) of preparing the cell suspension 21 is performed after the step (S2) of preparing the carriers 10 in the flowchart in FIG. 7A, but the carriers 10 and the suspension may be prepared at the same time, or the cell suspension 21 may be prepared before the carriers 10.

(Carrier)

The carrier 10 is not restricted. A carrier including a magnetic portion 12, formed only in a part of the carrier, and a cell holder 11 configured to hold cells 20 can be used. When the magnetic portion 12 is positioned only in a part of the carrier 10, the culture carriers can more easily be arranged in a specific orientation by the application of the magnetic field 51 in step (B) than when the entire carrier 10 is the magnetic portion 12. Consequently, a cell structure 100 with a complex structure can more efficiently be produced. In other words, use of the carrier 10 enables suitable production of a cell structure 100 having a structure in which directionality is important. Use of the carrier 10 also eliminates the need for directly magnetizing the cells 20 and is therefore less invasive to the cells.

The cell holder 11 has the property of holding cells 20. In the present application, the holding of cells by the cell holder 11 encompasses not only the cells 20 being joined to the cell holder 11 but also being buried or the like in the cell holder 11. The cell holder 11 is, for example, formed by solidifying a sol that has a cell holding property. In the present application, a sol that has cell holding property refers a sol to which the cells 20 can join when the sol is solidified, a sol into which the cells 20 can be buried, or the like. The cell holder 11 can, for example, be configured by a hydrogel and in particular preferably has high biocompatibility. Examples of the base material used to form the cell holder 11 include a polysaccharide such as agarose, alginic acid, or hyaluronic acid; a biopolymer forming an extracellular matrix such as elastin or collagen; a modified product of a biopolymer such as gelatin; a soluble basement membrane preparation such as Matrigel® (Matrigel is a registered trademark in Japan, other countries, or both) or Geltrex® (Geltrex is a registered trademark in Japan, other countries, or both) extracted from cells or tissues; and a synthetic polymer such as polyethylene glycol. A hydrogel has high affinity with the cells 20 and is therefore preferably used as the base material to form the cell holder 11. By virtue of being non-toxic and activating the cells 20, an extracellular matrix is more preferably used as the base material to form the cell holder 11.

The magnetic portion 12 has the property of being attracted to the magnetic field 51 when the magnetic field 51 is applied. The magnetic portion 12 can, for example, be a gel that contains magnetic particles and can be formed by kneading magnetic particles into a gel. Alternatively, the magnetic portion 12 may be formed by inserting a magnetic body into the carrier 10. The magnetic particles can be magnet powder, iron powder, or the like. The magnetic body may be a magnet, an iron core, or the like. The gel can, for example, be formed from a hydrogel and in particular preferably has high biocompatibility. Examples of the material that can form the gel include a polysaccharide such as agarose, alginic acid, or hyaluronic acid; a biopolymer forming an extracellular matrix such as elastin or collagen; a modified product of a biopolymer such as gelatin; a soluble basement membrane preparation such as Matrigel® or Geltrex® extracted from cells or tissues; and a synthetic polymer such as polyethylene glycol. The magnetic portion 12 can be formed from a gel that has a cell holding property to provide the magnetic portion 12 with the properties of the cell holder 11 as well. In other words, a member that is both the magnetic portion 12 and the cell holder 11 can be formed by including magnetic particles or the like in a gel that has a cell holding property and then magnetizing the gel.

The carrier 10 may have any shape, such as a column, a sphere, a sheet, or a fibrous shape and may be selected in accordance with the shape of the cell structure 100 to be produced. In an embodiment, the carrier 10 is columnar and includes the magnetic portion 12 towards one end from the center in the height direction, with the cell holder 11 extending in the height direction. By the carrier 10 being columnar and including the magnetic portion 12 towards one end from the center in the height direction, the culture carriers can be stood upright in the culture container 40 and arranged easily in step (B), described below. By the carrier 10 including the cell holder 11 that extends in the height direction, a plurality of cells 20 can be held in a stacked state along the height direction of the carrier 10. Accordingly, by culturing the cells 20 in the below-described step (C) while the cells 20 are held, a thick cell structure 100 with stacked cells 20 can be produced efficiently. The thickness of the cell structure 100 to be produced can be adjusted as appropriate by adjusting the range over which the cell holder 11 extends and the range over which cells 20 are held on cell holder 11. In an example, a cell structure 100 having three to four layers of stacked cells 20 can be produced.

Figure 2A:
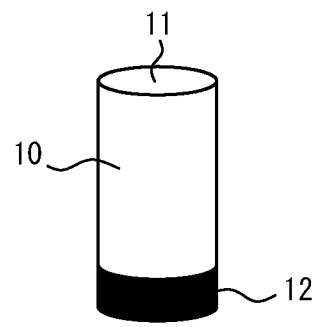
FIGS. 2A to 2C illustrate examples of the shape of a carrier, where
Figure 2B:
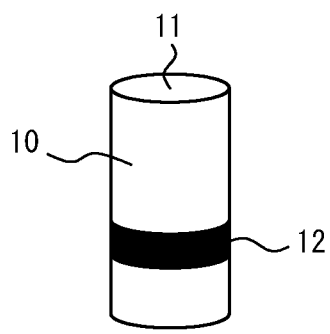
Figure 2C:
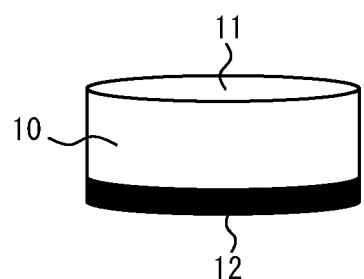

Any columnar carrier may be used, such as a carrier 10 with the shapes illustrated in FIGS. 2A to 2C. In the example in FIG. 2A, the carrier 10 overall has a columnar shape, with the magnetic portion 12 formed at one end, and the cell holder 11 extending in the longitudinal direction. The magnetic portion 12 need not be formed at the end. For example, the magnetic portion 12 is formed towards one end from the center in the height direction in the example illustrated in FIG. 2B. The overall shape of the carrier 10 is not restricted. For example, the carrier 10 may have a columnar shape with the transverse direction in the height direction, as in the example illustrated in FIG. 2C. In the example illustrated in FIG. 2C, the carrier 10 has the magnetic portion 12 formed at one end in the transverse direction, and the cell holder 11 extends in the longitudinal direction. When carriers 10 with the shape illustrated in FIG. 2C are used, the carriers 10 can be arranged stably with the magnetic field 51. As another example, the magnetic portion 12 may be formed only near the center of the carrier 10.

(Preparation of Carrier Suspension)

In step (A) of an embodiment, the carriers 10 are suspended in a cell-compatible liquid in the culture container 40, for example, to obtain a carrier suspension. A buffer solution such as phosphate buffered saline, a liquid culture medium such as Eagle's minimum essential medium, or the like can be used as the cell-compatible liquid. Methods that can be used to suspend the carriers 10 in the cell-compatible liquid include stirring, ultrasonic dispersion, and aeration.

The carriers 10 can be suspended directly in the cell suspension 21, described below, without preparation of a carrier suspension in step (A).

The cells 20 may be prokaryotic cells or eukaryotic cells. The eukaryotic cells may be cells of mammals, such as humans or mice, or cells derived from other vertebrates. In addition, the cells 20 may be stem cells such as embryonic stem cells, induced pluripotent stem cells, or mesenchymal cells. The cells 20 may be endodermal cells such as hepatocytes differentiated from a stem cell, mesodermal cells such as myocardial cells, or ectodermal cells such as nerve cells. The cells 20 may also be gene mutant cells derived from a cancerous tumor or the like. Apart from adhesive cells, floating cells such as blood cells can also be used as the cells 20 by being buried in the cell holder 11.

Cells 20 corresponding to the desired type of cell structure 100 can be used as the cells 20 held on the cell holder 11 of the carrier 10. One type of cells 20 may be held on the cell holder 11, or two or more types may be held. A cell structure 100 including two or more types of cells 20 can be produced when two or more types of cells 20 are held on the cell holder 11.

(Preparation of Cell Suspension)

The cell suspension 21 can be obtained by suspending the above-described cells in a cell-compatible liquid. A commercially-available liquid culture medium or the like can be used as the cell-compatible liquid. Methods that can be used to suspend the cells in the cell-compatible liquid include stirring, ultrasonic dispersion, and aeration.

(Cell Holding Step)

In step (A) of an embodiment, a carrier suspension and the cell suspension 21 are placed in contact in the culture container 40, for example, and cells 20 are held on the cell holder 11 of the carriers 10 to obtain the cell holding carriers 30. The conditions for holding cells 20 are preferably conditions that do not affect the cells 20. For example, a temperature condition of 37° C. or less is preferable for human cells. The cell density in the cell suspension 21 may be determined by the adhesiveness between the cell holder 11 and the cells 20. A high cell density is preferred in the case of low adhesiveness. The cell density in the cell suspension 21 may be low when the proliferation ability of the cells 20 is high.

(Container)

The container used in an embodiment may have any form and can be a typical culture container 40. The inner surface of the culture container 40 is preferably formed from material to which the cells 20 tend not to adhere. Forming the inner surface of the culture container 40 from a material to which the cells 20 tend not to adhere can prevent the cells 20 and the cell holding carriers 30 from adhering to an undesired portion of the inner surface of the culture container 40.

<Step (B)>

In step (B), the magnetic field 51 is applied to arrange the plurality of culture carriers in the culture container 40, Specifically, in step (B), the magnetic field 51 is applied by bringing the magnet 50 close to the bottom of the culture container 40 from below to attract the magnetic portion 12 of the carriers 10 to the portion where the magnetic field 51 is applied, thereby arranging the culture carriers that include the cell holding carriers 30 inside the culture container 40.

The arrangement of the culture carriers may be performed in the liquid phase or in the gas phase. In other words, the inside of the culture container 40 at the time of step (B) may or may not be filled with a liquid, such as a liquid culture medium.

An electromagnet or a permanent magnet can be used as the magnet 50. Use of an electromagnet facilitates application and removal of the magnetic field 51. Use of a permanent magnet enables the magnetic field 51 to be applied stably.

The culture carriers can be arranged as desired by adjustment of the pattern for applying the magnetic field 51 in step (B). This enables free control of the structure of the cell structure 100 to be produced by the method of producing a cell structure according to the present embodiment. For example, the distance between the arranged culture carriers can be the distance at which the cells 20 come into contact with each other. In cases such as formation of a cell structure 100 that includes neurites, for example, the culture carriers can be arranged so that the cells 20 are separated from each other. If at least a portion of the cells 20 are in contact between culture carriers, the time required for cell-cell adhesion can be shortened, enabling high-throughput production of the cell structure 100.

The magnetic field 51 is used for arrangement in step (B), enabling high-throughput production of the cell structure 100. Furthermore, the magnetic field 51 often has no adverse effect on the cells 20. The method of producing a cell structure according to the present embodiment is therefore not invasive to the cells 20.

Step (B) may include a step (b1) of applying vibration to the culture container 40. Arrangement of the culture carriers while vibration is applied to the culture container 40 can achieve suitable arrangement of the culture carriers. When vibration is applied to the culture container 40, culture carriers that were not arranged as desired temporarily break free from the hold of the magnetic field 51 and are then rearranged. The culture carriers can therefore be precisely arranged, reducing the variation in the shape of the cell structure 100 to be produced.

In step (B), the vibration may be switched on and off while the magnetic field 51 continues to be applied. When the vibration is switched on and off while the magnetic field 51 continues to be applied in step (B) in this way, the culture carriers that were not arranged as desired can be rearranged, the culture carriers can then be fixed by the magnetic field 51 in a temporary state without vibration, and vibration can subsequently be applied again as necessary. The risk of the properly arranged culture carriers becoming misaligned due to the vibration can therefore be reduced.

When the vibration can be switched on and off, step (B) may include setting the magnetic flux density of the magnetic field 51 while the vibration is applied to be lower than the magnetic flux density of the magnetic field 51 before the vibration is applied. When the magnetic flux density of the magnetic field 51 while the vibration is applied is set to be lower than the magnetic flux density of the magnetic field 51 before the vibration is applied in step (B) in this way, the hold of the magnetic field 51 on the culture carriers that were not arranged as desired can be temporarily weakened during vibration. The application of vibration therefore facilitates movement of the culture carriers that were not arranged as desired, so that these culture carriers can be rearranged efficiently, reducing the variation in the shape of the cell structure 100 to be produced.

Furthermore, step (B) may include a step (b2) of removing any unarranged culture carriers. Any removal method may be used, but the removal method is preferably gentle. Examples include turning the culture container 40 upside down while the magnetic field 51 is applied to the bottom of the culture container 40, adding a cleaning fluid, and the like. When unarranged culture carriers are removed in step (B) in this way, the shape of the cell structure 100 can be controlled precisely. The removed culture carriers may be reused in production of cell structures 100. Reuse of the culture carriers can reduce the cost of producing the cell structures 100.

<Step (C)>

In step (C), cells 20 held on the cell holders 11 of the culture carriers are cultured while the culture carriers are maintained in the arranged state in the culture container 40. Culturing leads to cell-cell adhesion between the cells 20 held on the cell holder 11 of nearby culture carriers. This results in a cell structure 100 in which the cells 20 held on the cell holders 11 are adhered to each other.

An appropriate culture medium for the type of cells 20 can be chosen to culture of the cells 20. For example, if the cells 20 are hepatocytes, a liquid culture medium (culture medium 41) such as a medium for hepatocytes can be used. Examples of culture media for hepatocytes include HepatoZYME. The culturing may be performed in step (C) after an operation for further holding cells 20 on the cell holders 11 of the arranged culture carriers. The cells 20 may be held on the cell holders 11 of the arranged culture carriers by an operation similar to the above-described operation to hold cells 20 on the carriers 10 in step (A).

In step (C), the cells 20 may be cultured while the magnetic field 51 is applied or cultured after application of the magnetic field 51 is stopped. Culturing is preferably performed in step (C) while the magnetic field 51 is applied. Culturing while the magnetic field 51 is applied can prevent misalignment of the culture carriers during culturing.

(Cell Structure)

In addition to a cell structure 100 with a spherical, columnar, or other such three-dimensional shape, a planar, sheet-shaped cell structure 100 can also be produced in step (C). A cell structure 100 including a three-dimensional structure that is planar and has sweat glands, pores, and the like in various places, such as skin tissue, can also be favorably produced.

The carrier 10 and the magnetic portion 12 do not adversely affect many assays. Therefore, the produced cell structure 100 can be used as is in many assays, without removal of the carriers 10 and the magnetic portions 12 from the cell structure 100. Not removing the magnetic portions 12 from the cell structure 100 facilitates fixing of the cell structure 100 by the magnetic field 51 and transportation of the cell structure 100.

Stopping application of the magnetic field 51 can cause the produced cell structure 100 to float in the culture container 40 for collection. This makes it unnecessary to perform potentially damaging treatment on the cell structure 100, such as enzyme treatment, when the cell structure 100 is collected. The cell structure 100 can therefore be collected in an intact state.

<Step (D)>

The method of producing a cell structure may further include a step (D) of removing the magnetic portions 12 from the cell structure 100 after step (C). When the magnetic portions 12 are removed from the cell structure 100, a cell structure 100 with less material other than the cells 20 can be produced. The magnetic portions 12 are preferably removed with step (D) when the cell structure 100 is to be used for purposes related to magnetic fields, such as measuring the produced cell structure 100 by NMR.

Figure 5A:
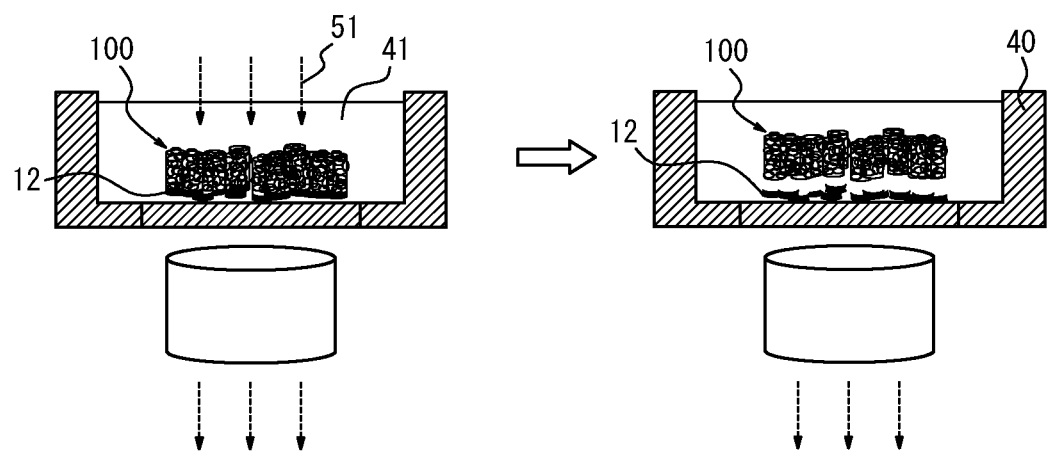
FIG. 5A illustrates an example method of removing the magnetic portion from the cell structure.

The magnetic portions 12 may, for example, be removed in the manner illustrated in FIG. 5A. The magnetic portions 12 and the cell holder 11 are formed from different materials in the example in FIG. 5A. Specifically, the magnetic portions 12 are produced from agarose and magnetic particles, and the cell holder 11 is produced from collagen. In the example in FIG. 5A, a substance that can decompose only the material forming the magnetic portions 12, such as an agarose degrading enzyme, is added to the culture medium 41 and reacted while the magnetic field 51 is applied to the produced cell structure 100. The magnetic portions 12 are removed from the cell structure 100 by decomposition of the material forming the magnetic portion 12, and the cell structure 100 is caused to float in the culture container 40. The substance that can decompose only the material forming the magnetic portions 12, such as an agarose degrading enzyme, may be added and reacted while the magnetic field 51 is applied or without application of the magnetic field 51.

<Step (E)>

Figure 5B:
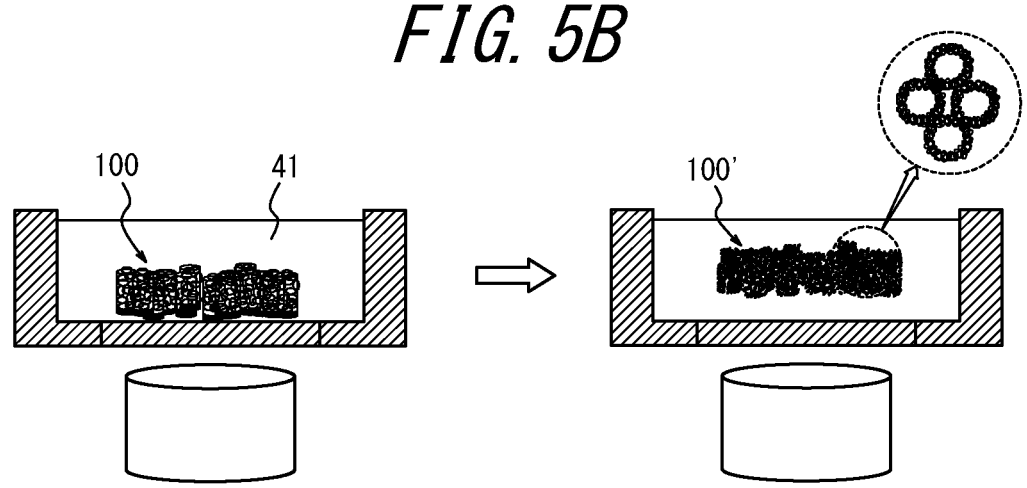
FIG. 5B illustrates an example method of removing the carrier from the cell structure.

The method of producing a cell structure may further include a step (E) of removing the carriers 10 from the cell structure 100. When the carriers 10 are removed from the cell structure 100 in this way, the portions that were occupied by the carriers 10 become hollow. This enables production of a cell structure 100 with a complex structure, such as a highly oxygen-permeable cell structure 100 with many empty spaces. When the carriers 10 are removed from the cell structure 100, a cell structure 100 with less material other than the cells 20 can be produced. In an example, the carriers 10 are formed from a material decomposable in an enzyme, and the carriers 10 are removed by being decomposed by enzyme treatment after production of the cell structure 100. Alternatively, a stimulus responsive polymer layer that reacts to a stimulus such as temperature may be formed on the cell holder 11 of the carrier 10, and the cells 20 and carriers 10 may be separated by the application of the stimulus, such as temperature, after production of the cell structure 100. A redox reaction may be used to decompose the carriers 10, thereby removing the carriers 10 from the cell structure 100. The carriers 10 are preferably removed by being decomposed by an enzyme, or by being separated from the cell structure 100 by the application of an external stimulus to carriers 10 that have been surface modified with a stimulus responsive polymer, since these methods are not toxic to the cells 20. FIG. 5B schematically illustrates an example of step (E). In the example in FIG. 5B, the carriers 10 are mainly produced from collagen. After culturing is complete, a collagen degrading enzyme is added to the culture medium 41 and reacted. The carriers 10 are removed from the cell structure 100 by being decomposed by the collagen degrading enzyme, yielding a highly oxygen-permeable cell structure 100' with many empty spaces. The collagen degrading enzyme may be added and the collagen degrading reaction may be performed while the magnetic field 51 is applied or without application of magnetic field 51.

In the method of producing a cell structure, the above-described steps (A) to (C), and optional steps such as step (D) or step (E), may be repeated multiple times. A cell structure 100 with a more complex structure can be formed by repetition of the above-described steps (A) to (C) and other optional steps. In an example, after the culture carriers are arranged by application of the magnetic field 51 in step (B), the unarranged culture carriers are removed by step (b2). After cells 20 are optionally cultured, the pattern of the magnetic field 51 regions are then changed, culture carriers are added again to the culture container 40 and arranged by the magnetic field 51, and the cells 20 are cultured. A cell structure 100 with a complex structure not obtainable with only a one-stage arrangement of the culture carriers can thereby be produced.

Second Embodiment

Figure 7B:
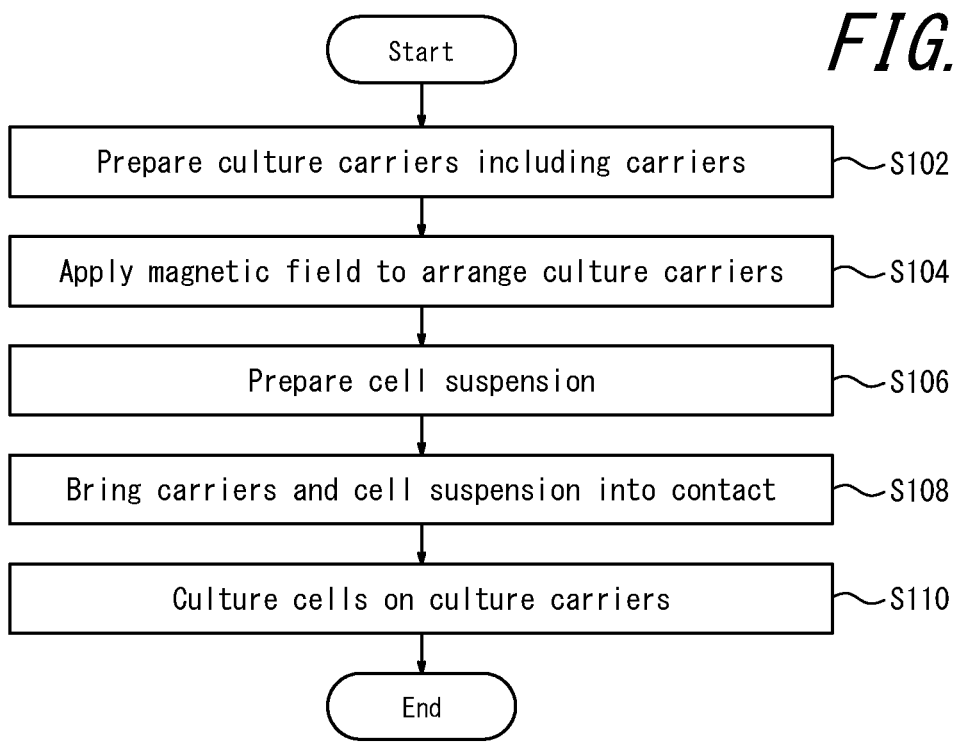

FIG. 7B illustrates another example of the flow in a method of producing a cell structure. Since examples of carriers 10, a carrier suspension, cells 20, a cell suspension 21, and a culture container 40 are the same as in the first embodiment, a description thereof is omitted.

The method of producing a cell structure illustrated in FIG. 7B includes a step (A) of preparing a plurality of culture carriers including non-cell holding carriers 10, a step (B) of applying a magnetic field 51 to arrange the plurality of culture carriers in a culture container 40, a step (b3) of holding cells 20 on cell holders 11 of the arranged culture carriers, and a step (C) of culturing cells 20 held on the culture carriers while maintaining the culture carriers in an arranged state in the culture container 40. The method of producing a cell structure may include the above-described step (D) or step (E), like the first embodiment. Since the step (D) and step (E) can be performed in the same way as in the first embodiment, a description thereof is omitted.

<Step (A)>

In step (A), a plurality of culture carriers including carriers 10 (non-cell holding carriers) each including a magnetic portion 12 and a cell holder 11 are prepared.

The carriers 10 can be produced by any method, such as the below-described method of producing carriers. Cell holding carriers 30 may be included in the culture carriers.

<Step (B)>

Apart from arranging culture carriers that include the non-cell holding carriers 10, step (B) can be performed similarly to step (B) in the above-described first embodiment.

<Step (C)>

In step (C), cells 20 are held on the cell holders 11 of the arranged culture carriers (step (b3)), and the cells 20 held on the culture carriers are then cultured while the culture carriers are maintained in the arranged state in the culture container 40.

Apart from the culture carriers being fixed by application of a magnetic field 51, the cells 20 may be held on the cell holders 11 of the arranged culture carriers in the same way as the cells 20 are held on the cell holders 11 of the carriers 10 in step (A) of the above-described first embodiment.

In step (b3), cells 20 are held on the cell holders 11 of the non-cell holding carriers 10 included in the culture carriers arranged in step (B), and the cell holding carriers 30 are arranged inside the culture container 40.

The culturing can be performed in the same way as in step (C) of the first embodiment.

In the second embodiment, as in the above-described first embodiment, a cell structure 100 organized into a desired shape, such as a sheet, a tube, or a sphere, can be produced at high throughput and little invasiveness to the cells. Furthermore, arrangement of the culture carriers before the step (b3) of holding the cells makes it unnecessary to manage the operating conditions to avoid adverse effects on cells in step (B) of arranging the culture carriers. This simplifies the operations of step (B).

The first and second embodiments have been described, but the method of producing a cell structure of the present disclosure is not limited to these embodiments.

Specifically, in the method of producing a cell structure, two or more types of carriers 10 may be used. When two or more types of carriers 10 are used, the method of holding the cells 20, the method of arranging the culture carriers, and the like can be different for each type of carrier 10. Therefore, the use of two or more types of culture carriers enables production of a cell structure 100 with a more complex structure than when only one type of culture carrier is used. For example, the use of two or more types of columnar culture carriers with different heights enables production of a cell structure 100 that has different thicknesses in different parts. At least one selected from the group consisting of the shape, material, specific gravity, position of the magnetic portion 12, magnetic strength of the magnetic portion 12, and area of the cell holder 11 can differ among the two or more types of culture carriers.

Figure 3A:
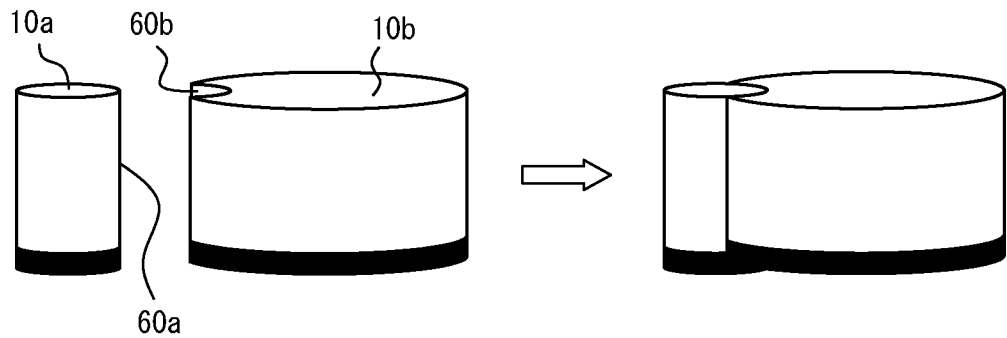
FIGS. 3A and 3B illustrate examples of combining carriers, where

The culture carrier may include an engaging portion for culture carriers to engage with each other, as illustrated in FIG. 3A, for example. When the culture carrier includes an engaging portion, a plurality of culture carriers can be arranged by the engaging portions engaging with each other in step (B). As a result of the culture carrier including an engaging portion, arrangement is affected not only by the magnetic field 51 but also by the engagement of the engaging portions. The culture carriers can therefore be arranged in a more complex shape than when only being arranged using the magnetic field 51, enabling production of a cell structure 100 with a more complex structure. The engagement of culture carriers with each other also enables more accurate arrangement than when the culture carriers are arranged only by the magnetic field 51. Furthermore, since the engaging portions of the culture carriers engage with each other, the arranged state of the culture carriers can be maintained more easily. In the example in FIG. 3A, a wall surface 60a of a carrier 10a and a recess 60b provided on a carrier 10b serve as engaging portions, and the wall surface 60a engages with the recess 60b in step (B). Culture carriers including an engaging portion are not, however, limited to the illustrated example.

Figure 3B:
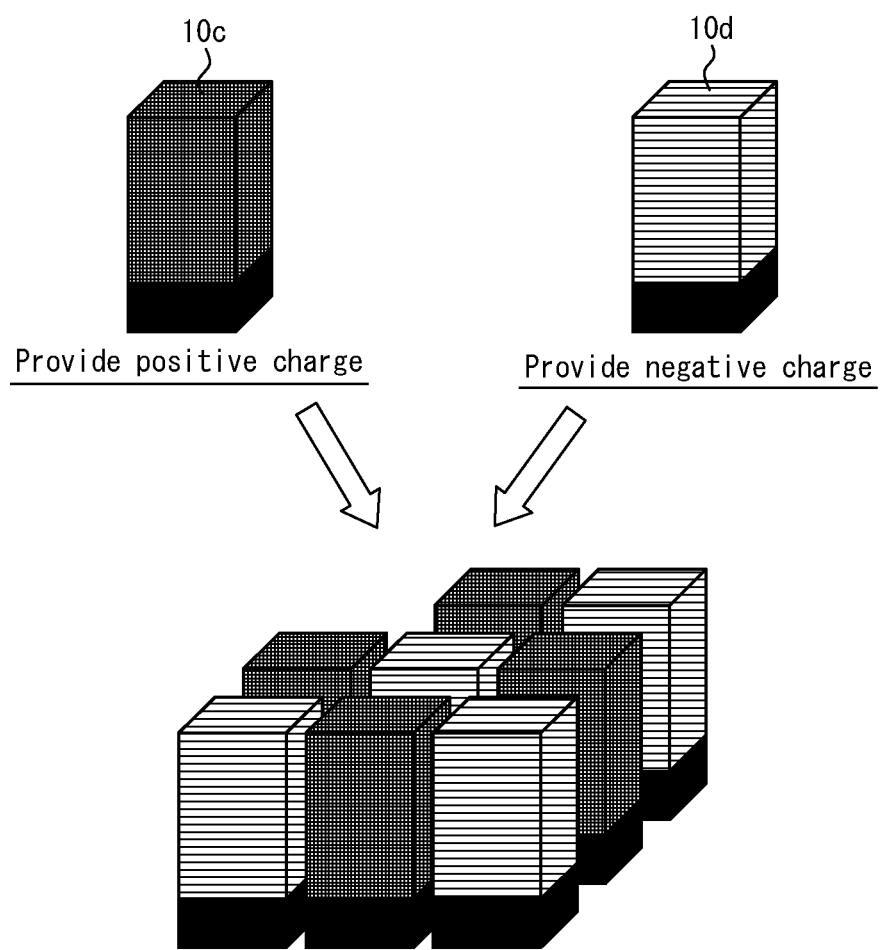

At least one characteristic may differ between two or more types of the culture carriers, and the culture carriers may exhibit affinity or repellence towards each other due to the characteristic, as illustrated in FIG. 3B, for example. When at least one characteristic differs between two or more types of culture carriers, and the culture carriers exhibit affinity or repellence towards each other due to the characteristic, then the arrangement of the culture carriers is affected not only by the magnetic field 51, but also by the affinity or repellence due to the differing characteristic. The culture carriers can therefore be arranged in a more complex shape than when only being arranged using the magnetic field 51, enabling production of a cell structure 100 with a more complex structure. Furthermore, when the culture carriers exhibit affinity or repellence towards each other, the arranged state of the culture carriers can be maintained more easily. In an example, at least one characteristic selected from the group consisting of hydrophobicity, hydrophilicity, the protein covering the surface of the carrier 10, and electric charge differs between two or more types of culture carriers. In the example in FIG. 3B, a positive charge is provided to a carrier 10c, whereas a negative charge is provided to a carrier 10d. In step (B), therefore, the carriers 10c and 10d electrically attract or repel each other so that the carriers 10c and 10d tend to be arranged alternately.

Figure 4:
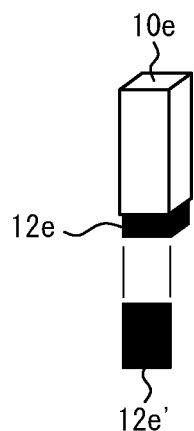
FIG. 4 illustrates a container that has a fitting portion and carriers capable of fitting into the fitting portion.
Figure 4:
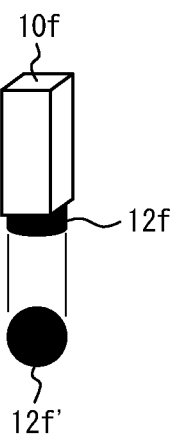
Figure 4:
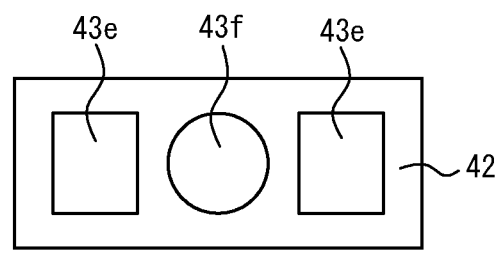
Figure 4:
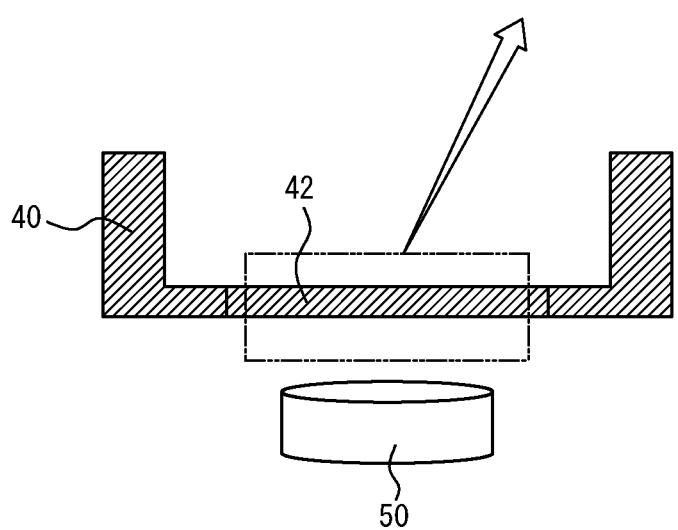

The culture container 40 may include a fitting portion onto which the culture carriers fit, as illustrated in FIG. 4. When the culture container 40 includes the fitting portion onto which the culture carriers fit, the culture carriers can be fitted onto the fitting portion and arranged in step (B). This enables formation of a cell structure 100 with a more complex pattern and enables more accurate arrangement of the culture carriers than in the case of arrangement using only the magnetic field 51. Furthermore, since the culture carriers are fitted onto the fitting portion of the culture container 40, the arranged state of the culture carriers can be maintained more easily. The fitting portion can have a shape corresponding to the type of culture carriers to be arranged. The fitting portion may have a shape into which at least a portion of the culture carriers can fit.

In the example illustrated in FIG. 4, a carrier 10e and a carrier 10f are configured so that shapes 12e' and 12f' of the bottoms of the magnetic portions 12e and 12f differ from each other. Fitting portions 43e and 43f into which 12e' and 12f' fit are formed on the bottom surface 42 of the culture container 40. Therefore, when the magnetic field 51 is applied in step (B), 12e' fits into the fitting portion 43e and 12f' fits into the fitting portion 43f, accurately arranging the carriers 10e and 10f and facilitating maintenance of the arranged state.

Figure 6:
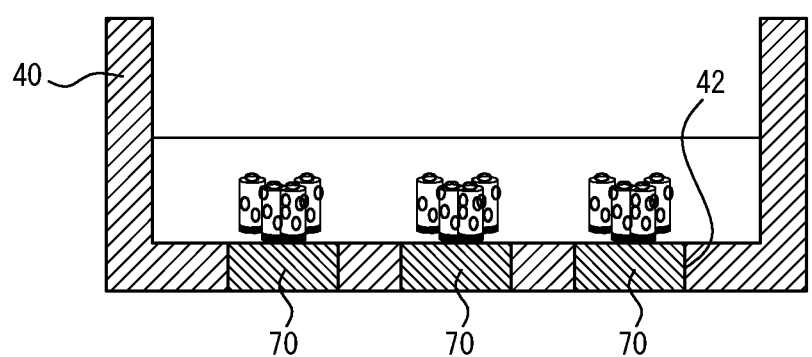
FIG. 6 schematically illustrates an example of arranging culture carriers in a plurality of regions separated from each other.

As illustrated in FIG. 6, the magnetic field 51 may be applied to a plurality of regions 70 separated from each other in the culture container 40, and a plurality of culture carriers may be arranged in the plurality of regions in step (B). When the magnetic field 51 is applied to the plurality of regions 70 separated from each other in the culture container 40 in this way, a plurality of culture carriers are arranged in regions having, as an outer periphery, the range of the magnetic field that has the minimum strength capable of fixing the carriers 10. Consequently, a plurality of cell structures 100 can be produced simultaneously in one culture container, enabling high-throughput production of cell structures 100. The intervals between the plurality of regions 70 to which the magnetic field 51 is applied need not be equal. For production efficiency, however, intervals maximizing the number of regions 70 per unit area of the bottom surface 42 are preferably selected.

[Method of Producing Carriers]

The carriers 10 that can be used in the above-described method of producing a cell structure of the present disclosure are not restricted and can be suitably produced using the method of producing carriers of the present disclosure.

The method of producing carriers according to an embodiment of the present disclosure is a method of producing the above-described carriers 10. The method includes forming, in a mold, a layer including a sol containing magnetic particles and a layer including a sol having a cell holding property, and solidifying each sol in the mold. The layer including the sol containing magnetic particles and the layer including the sol having a cell holding property respectively become the magnetic portion 12 and the cell holder 11 as a result of the sols solidifying. This production method enables simple production of carriers 10 to be used in the method of producing a cell structure according to various embodiments.

Any type of sol may be used. Examples include a polysaccharide such as agarose, alginic acid, or hyaluronic acid; a biopolymer forming an extracellular matrix such as elastin or collagen; a modified product of a biopolymer such as gelatin; a soluble basement membrane preparation such as Matrigel® or Geltrex® extracted from cells or tissues; and a synthetic polymer such as polyethylene glycol. Different sols may be used to form the cell holder 11 and the magnetic portion 12. The cells 20 may be mixed into the sol before solidifying the sol to hold the cells 20 on the cell holder 11 while simultaneously forming the cell holder 11. When the sol is solidified after the cells 20 are mixed into the sol in this way, a highly concentrated cell suspension 21 need not be used, unlike when the cell suspension 21 is mixed with the carriers 10 for the cells 20 to be held after the carriers 10 are formed. This prevents the cells 20 from being wasted.

Any mold can be used, but to facilitate extraction of the produced carriers 10, the mold is preferably made of an elastic material, such as silicone rubber composed of polydimethylsiloxane or the like.

[Kit]

A kit for producing a cell structure according to an embodiment includes culture carriers including at least one of a carrier 10 and a cell holding carrier 30, the carrier 10 including a magnetic portion 12 formed only in a part of the carrier 10 and a cell holder 11 configured to hold cells 20, and the cell holding carrier 30 being formed by cells 20 being held on the cell holder 11 of the carrier 10. Use of this kit for production enables simple implementation of the method of producing a cell structure according to an embodiment of the present disclosure. Additionally, the kit for producing a cell structure according to an embodiment may include at least one selected from the group of an instruction manual for the kit, a culture container 40, a magnetic field application device, and a cell-compatible liquid. Instead of the instruction manual, the kit for producing a cell structure may include a document listing a method for downloading the instruction manual from a server.

EXAMPLES

Polydimethylsiloxane (PDMS) was used to produce a mold with cylindrical, non-through holes. A Matrigel® solution (produced by BD Biosciences) with magnetic particles mixed therein was introduced, using an inkjet spotter, to approximately 1/10 the height of the non-through holes. Next, a Matrigel solution (sol) was layered on top, using the inkjet spotter, to approximately 9/10 the height of the non-through holes. The mold was then placed in an incubator at 37° C., and the Matrigel solution was solidified. Cylindrical carriers each having a magnetic portion formed by magnetic particles buried near one end, with the entire surface of each carrier serving as a cell holder, were thus obtained. Taking advantage of how PDMS is elastic, tension was applied to the mold to expand the hole diameter of the non-through holes and remove the carriers from the non-through holes. The removed carriers were dispersed in a liquid culture medium.

HepG2 cells, which are a cell line derived from liver cancer, were cultured on a culture dish. The cells were detached from the culture dish with a sufficient amount of enzyme. The detached cells were suspended in a liquid culture medium to obtain a cell suspension.

The liquid culture medium with the dispersed carriers was introduced into culture wells (culture container), and the cell suspension was mixed therein. The mixed solution was incubated to hold cells on the cell holders of the carriers, yielding cell holding carriers. A magnetic field was applied by placing a magnet by the outside of the bottom surface of the culture well to align the cell holding carriers, with the magnetic portions facing the bottom surface of the culture well, and to place the cell holding carriers close to each other.

The liquid culture medium was extracted, thus removing cells not fixed to carriers. Next, fresh culture medium was added. The cell holding carriers arranged by the magnetic field 51 and placed close to each other were cultured while the culture medium was exchanged as appropriate. The cells proliferated, cell-cell binding occurred, and the cell holding carriers became integrated by cell-cell adhesion. A thick sheet-like cell structure was thereby formed. Application of the magnetic field was suspended by moving the magnet away from the culture wells. The formed tissue was detached from the bottom surface of the culture and collected.

INDUSTRIAL APPLICABILITY

A method of producing a cell structure, a carrier, and a method of producing a carrier according to the present disclosure can be used in fields such as regenerative medicine, disease modeling, drug efficacy tests, and safety tests.

The invention claimed is:

1. A method of producing a cell structure, the method comprising:
   a step A of preparing a plurality of culture carriers each comprising a cell holder configured to hold cells and a magnetic portion formed only in a part of the cell holder;
   a step B of applying a magnetic field to arrange the plurality of culture carriers in a container; and
   a step C of culturing cells held on the cell holder of the culture carriers while maintaining the culture carriers in an arranged state in the container,
   wherein the cells are held in the cell holder either one of in the step A or after the step B and before the step C, and
   the step B comprises a step b1 of applying vibration to the container such that at least a part of the plurality of culture carriers temporarily break free from a hold of the magnetic field and then rearranging the plurality of culture carriers in the container.

2. The method of producing a cell structure of claim 1, wherein each one of the culture carriers is columnar and includes the magnetic portion towards one end from a center in a height direction, and the cell holder extends in the height direction.

3. The method of producing a cell structure of claim 1, wherein the step B further comprises switching the vibration on and off while continuing to apply the magnetic field.

4. The method of producing a cell structure of claim 1, wherein the step B further comprises setting a magnetic flux density of the magnetic field while the vibration is applied to be lower than a magnetic flux density of the magnetic field before the vibration is applied.

5. The method of producing a cell structure of claim 1, wherein the step B further comprises a step b2 of removing unarranged culture carriers.

6. The method of producing a cell structure of claim 1, wherein two or more types of the culture carriers are used.

7. The method of producing a cell structure of claim 6, wherein at least one characteristic differs between the two or more types of the culture carriers, and the culture carriers exhibit affinity or repellence towards each other due to the characteristic.

8. The method of producing a cell structure of claim 1,
   wherein the plurality of culture carriers comprise engaging portions configured to engage with each other; and
   wherein the step B further comprises engaging the engaging portions with each other to arrange the plurality of culture carriers.

9. The method of producing a cell structure of claim 1,
   wherein the container comprises a fitting portion, and the culture carriers are configured to fit onto the fitting portion; and
   wherein the step B further comprises fitting the culture carriers onto the fitting portion to arrange the culture carriers.

10. The method of producing a cell structure of claim 1, further comprising a step D of removing the magnetic portion from the cell structure.

11. The method of producing a cell structure of claim 1, further comprising a step E of removing the culture carriers from the cell structure.

12. The method of producing a cell structure of claim 1, wherein the step B further comprises applying the magnetic field to a plurality of regions separated from each other in the container and arranging the plurality of culture carriers in the plurality of regions.

* * * * *